United States Patent
Shah et al.

(10) Patent No.: US 8,853,189 B2
(45) Date of Patent: Oct. 7, 2014

(54) ANTISPASMODIC 1,2-DIOLS AND 1,2,3-TRIOLS

(71) Applicants: Priti Sanghvi Shah, Rockaway, NJ (US); Mandar V. Shah, Rockaway, NJ (US)

(72) Inventors: Priti Sanghvi Shah, Rockaway, NJ (US); Mandar V. Shah, Rockaway, NJ (US)

(73) Assignee: Prima Innovations, LLC, Wayne, NJ (US)

( * ) Notice: Subject to any disclaimer, the term of this patent is extended or adjusted under 35 U.S.C. 154(b) by 0 days.

(21) Appl. No.: 13/798,822

(22) Filed: Mar. 13, 2013

(65) Prior Publication Data

US 2013/0324504 A1     Dec. 5, 2013

Related U.S. Application Data

(60) Provisional application No. 61/653,737, filed on May 31, 2012.

(51) Int. Cl.

| | |
|---|---|
| *A61K 31/047* | (2006.01) |
| *A61K 45/06* | (2006.01) |
| *A61K 31/196* | (2006.01) |
| *A61K 31/137* | (2006.01) |
| *A61K 31/421* | (2006.01) |
| *A61K 31/593* | (2006.01) |

(52) U.S. Cl.
CPC ............... *A61K 31/047* (2013.01); *A61K 45/06* (2013.01); *A61K 31/137* (2013.01); *A61K 31/196* (2013.01); *A61K 31/421* (2013.01); *A61K 31/593* (2013.01)
USPC ............ 514/167; 514/738; 514/171; 514/567

(58) Field of Classification Search
CPC ...................... A61K 31/047; A61K 31/196
See application file for complete search history.

(56) References Cited

U.S. PATENT DOCUMENTS

| | | | |
|---|---|---|---|
| 3,655,776 A | 4/1972 | Lafon | |
| 4,076,937 A | 2/1978 | Vigelius et al. | |
| 4,119,730 A | 10/1978 | Deininger et al. | |
| 4,537,776 A | 8/1985 | Cooper | |
| 4,552,872 A | 11/1985 | Cooper et al. | |
| 4,677,101 A | 6/1987 | Claremon et al. | |
| 5,374,661 A * | 12/1994 | Betlach, II | 514/772.4 |
| 6,207,852 B1 | 3/2001 | Aberg et al. | |
| 6,277,892 B1 | 8/2001 | Deckner et al. | |
| 7,141,696 B2 | 11/2006 | Aberg et al. | |
| 8,236,348 B2 | 8/2012 | Gin et al. | |
| 8,318,973 B2 | 11/2012 | Bezwada | |
| 8,329,445 B2 | 12/2012 | Frost | |
| 8,362,091 B2 | 1/2013 | Tamarkin et al. | |
| 2006/0018867 A1 | 1/2006 | Kawarski et al. | |
| 2006/0292223 A1 | 12/2006 | Woolfson et al. | |
| 2007/0207105 A1 | 9/2007 | Winn | |
| 2009/0143489 A1 | 6/2009 | Winn | |
| 2009/0182054 A1 * | 7/2009 | Zhang | 514/574 |
| 2009/0221716 A1 | 9/2009 | Faergemann et al. | |
| 2011/0104085 A1 | 5/2011 | Klug et al. | |
| 2012/0093882 A1 | 4/2012 | Roy et al. | |
| 2012/0213717 A1 | 8/2012 | Shah | |
| 2012/0321698 A1 | 12/2012 | Narain et al. | |

FOREIGN PATENT DOCUMENTS

| | | |
|---|---|---|
| CA | 2768423 A1 | 8/2012 |
| EP | 0043738 A2 | 1/1982 |
| EP | 0621263 A2 | 10/1994 |
| EP | 0868915 A1 | 10/1998 |
| EP | 2514407 A1 | 10/2012 |
| FR | 2068442 | 11/1969 |
| WO | WO 00/30715 A1 | 6/2000 |
| WO | WO 01/00139 A1 | 1/2001 |
| WO | WO 02/051395 A1 | 7/2002 |
| WO | WO 2008/049020 A2 | 4/2008 |
| WO | WO 2010/050889 A1 | 5/2010 |

OTHER PUBLICATIONS

Dale in www.ispine.org/forum/ispine/1608-anti-inflammatories.html (published: Aug. 2, 2009), retrieved from the internet Jan. 18, 2014.*
See et al. in American Family Physician 78(3), 365-370 (2008).*
Flygare et al. in Clinical Rheumatology, 7(1), 124-125.*
Hexylene glycol in http://www.sigmaaldrich.com/catalog/product/aldrich/112100?lang=en&region=US (retrieved from the internet Jan. 18, 2014).*
Akaneme, F.I. "Identification and Preliminary Phytochemical Analysis of Herbs that Can Arrest Threatened Miscarriage in Orba and Nsukka Towns of Enugu State," *African J. of Biotechnology*, 2008, 7, 6-11.
Fusi F.; Marazova, K.; Pessina, F.; Gorelli, B.; Valoti, M.; Frosini, M.; Sgaragli, G. "On the Mechanisms of the Antipasmodic Action of Some Hindered Phenols in Rat Aorta Rings," *EP J of Pharmacology*, 2000, 394, 109-115.
Massey, T.; Derry, S.; Moore R.A.; McQuay, H.J. *The Cochrane Collaboration*, 2010, John Wiley & Sons, Ltd.

(Continued)

*Primary Examiner* — Dennis Heyer
(74) *Attorney, Agent, or Firm* — Brinks Gilson & Lione

(57) ABSTRACT

The present invention is directed to pharmaceutical compositions comprising antispasmodic $C_4$-$C_8$ aliphatic-1,2-diols and $C_4$-$C_8$ aliphatic-1,2,3-triols and their use to relieve the spasms associated with pain. These agents may be administered topically or orally and may be combined with anti-inflammatory agents such as a non-steroidal anti-inflammatory drug or a corticosteroid. Administration of the $C_4$-$C_8$ aliphatic-1,2-diols and $C_4$-$C_8$ aliphatic-1,2,3-triols with vitamin $D_3$ is indicated for conditions such as bone loss, weight gain and autoimmune diseases such as lupus and rheumatoid arthritis.

17 Claims, No Drawings

(56) References Cited

OTHER PUBLICATIONS

Patel, R.K.; Leswell, P.F. "Comparison of Ketoprofen, Piroxicam and Diclofenac Gels in the Treatement of Acute Soft-Tissue Injury in General Practice," *Clinical Therapeutics*, 1996, 18, 497-507.

"Nimulid™ Transgel " www.panaceabiotec.com/licensing/nimulid_transgel.pdf, 2010, 5 pages.

Annex to Form PCT/ISA/206 Communication Relating to the Results of the Partial International Search dated Jul. 3, 2013 for co-pending International Patent Application No, PCT/US2013/042583, pp. 3-4.

* cited by examiner

ANTISPASMODIC 1,2-DIOLS AND 1,2,3-TRIOLS

RELATED APPLICATIONS

This application claims the benefit of U.S. Provisional Application No. 61/653,737 filed on May 31, 2012, the disclosure of which is incorporated herein by reference in its entirety.

BACKGROUND OF THE INVENTION

1. Field of the Invention

The present invention relates to the field of pharmaceutical compositions and their use to relieve the spasms associated with pain. It describes pharmaceutical compositions comprising an antispasmodic agent alone or in combination with analgesic agents such as a non-steroidal anti-inflammatory drug (NSAID) and/or pharmaceutically acceptable agents/excipients to relieve the spasms associated with pain.

The present invention provides a method for relieving spasms associated with pain wherein the pharmaceutical compositions comprising an antispasmodic agents are selected from a group consisting of a diol (with the total of 2 hydroxyl groups) or a triol (with a total of 3 hydroxyl groups) compound with carbon chain length of 4 to 8 and/or in combination with the analgesic agents, including NSAID agents, such as diclofenac, piroxicam, nimesulide, ketoprofen, ibuprofen, methyl salicylate; or steroidal agents, such as various anti-inflammatory corticosteroids, prednisone, etc.

2. Description of the Related Art

The majority of joint and muscle pain is associated with some kind of muscular spasms. Muscular spasm is defined by sudden involuntary contraction of a muscle or a group of muscles. These muscular spasms are associated with some kind of inflammation. Many times, the muscular inflammation is treated by oral non-steroidal agents (NSAIDs). However, utilizing oral dosage forms to treat localized join or muscle pain has a significant disadvantage of exposing the whole body to the drug. Topical application of anti-inflammatory agents offers the possibility of achieving local therapeutic benefit while reducing or eliminating the risk of systemic exposure and effects. As a result, diclofenac, piroxicam, nimesulide, ketoprofen, and hydrocortisone gel/cream/lotion/ointment have gained in popularity. While all of the anti-inflammatory compounds reduce the inflammation, they do little to reduce the muscle spasm.

U.S. Pat. No. 6,277,892 discloses an invention which relates to pharmaceutical compositions for topical application comprising a safe and effective amount of a pharmaceutical active, and from about 0.1% to about 10.0% of a high molecular weight cationic polymer. These compositions provide enhanced penetration of the pharmaceutical active. These compositions can also contain one or more additional humectants/moisturizers, many of which may also be useful as actives wherein the preferred humectants/moisturizers for use in the compositions of the present invention are the C3-C6 diols and triols. Especially preferred is the triol, glycerin.

EP 2340043 A1 discloses an invention which relates to a composition for improved transdermal drug delivery comprising a drug, a combination of at least two penetration enhancing agents, wherein at least one of the penetration enhancing agents is selected from the group consisting of esters of saturated or unsaturated fatty acids and lower alcohols, and iso-form alcohols; wherein at least one of the penetration enhancing agents is selected from the group consisting of aliphatic diols and triols; and wherein the components are present in a non-aqueous solvent system.

U.S. Pat. No. 8,236,348 discloses a dosage form wherein the dosage form is made adhesive by using a lower molecular weight hydrophilic polymer rather than by incorporation of additional polymers not contained within the wet matrix. When the dosage forms of the invention serve as transmucosal delivery systems, various carriers and additives may be incorporated as is well known in the art of transmucosal (e.g., buccal) drug delivery. Typical additives include permeation enhancers such as polyethylene glycol esters, long-chain fatty acid esters of diols and triols (e.g., glycerol monolaurate, propylene glycol monolaurate), lower alkanols, and the like.

SUMMARY OF THE INVENTION

The present invention relates to the field of pharmaceutical compositions and their use to relieve the spasms associated with pain. It describes methods of treating muscle spasms and pharmaceutical compositions comprising an antispasmodic agent alone or in combination with analgesic agents such as a non-steroidal anti-inflammatory drug (NSAID) and/or pharmaceutically acceptable excipients to relieve the spasms associated with pain.

The compositions of the present inventions comprise of at least one diol or triol compound with the purpose of relieving muscular spasm. This diol or triol compound may or may not be combined with other anti-inflammatory agent(s) or muscle relaxing agents.

The present invention provides the pharmaceutical compositions in the form of topical delivery, oral delivery in appropriate dosage forms, and injectable dosage forms. Suitable dosage forms include tablets, capsules, powders, aqueous liquids, solutions, microemulsions, nanoemulsion, nano reservoir system, in-situ gel drops, nanoparticulate system, vesicular systems such as liposomes, microspheres, niosomes, bioadhesive gel drops and the like.

In one aspect, the current invention provides a method of treating muscle spasm by administering to a patient one or more antispasmodic diols, triols, or mixtures thereof. The antispasmodic diols or triols for use according to the invention are $C_4$-$C_8$ aliphatic-1,2-diols or $C_4$-$C_8$ aliphatic-1,2,3-triols and may be administered in the form of a pharmaceutical composition. In certain embodiments, the invention provides methods of treating muscle spasm, pain and/or inflammation associated with the muscle spasm by administering one or more antispasmodic diols or triols with an anti-inflammatory agent. Other embodiments provide methods of treating muscle spasm and bone loss, weight gain, arthritis, or autoimmune disease by administering one or more antispasmodic diols or triols with vitamin $D_3$.

In another aspect, the invention provides pharmaceutical compositions comprising therapeutically effective amounts of the antispasmodic diols or triols and a pharmaceutically acceptable carrier. In certain embodiments, the present invention provides the pharmaceutical compositions for once-a-day, twice-a-day and/or thrice-a-day administration. These diols may be combined with the above mentioned anti-inflammatory agents in appropriate dosage forms.

In another aspect, the invention provides methods of manufacturing the pharmaceutical compositions of the invention.

DETAILED DESCRIPTION

In the current invention, series of diols and triols have been identified that can treat muscular spasm. When used with an anti-inflammatory agent, the diols and triols provide superior pain relief compared to when an anti-inflammatory agent is used alone. The diols and triols can be saturated, unsaturated, straight or branched chain aliphatic compounds. The minimum structural requirement for the diols is to have one hydroxyl group substituted on each of the first and second carbons of an aliphatic group (e.g., —CHOHCH$_2$OH). Likewise, the triols have one hydroxyl group substituted on each of the first, second, and third carbons of an aliphatic group (e.g., —CHOHCHOHCH$_2$OH). The aliphatic portion of the antispasmodic diols and triols includes 4-8 carbons. The other end of the carbon chain opposite the diol or triol moiety may be optionally derivatized.

The present invention provides a method for relieving spasms or spasms associated with pain wherein the pharmaceutical compositions comprise one or more antispasmodic agents selected from the group consisting of a diol (with the total of 2 hydroxyl groups) or a triol (with a total of 3 hydroxyl groups) compound with carbon chain length of 4 to 8 and/or in combination with the analgesic agents including NSAID agents, such as diclofenac, piroxicam, nimesulide, ketoprofen, ibuprofen, methyl salicylate; and/or steroidal agents, such as various anti-inflammatory corticosteroids, prednisone, etc.

The antispasmodic agents of the present invention are $C_4$-$C_8$aliphatic-1,2-diols and $C_4$-$C_8$aliphatic-1,2,3-triols. A "$C_4$-$C_8$aliphatic-1,2-diol," as used herein refers to a $C_4$-$C_8$alkane-1,2-diol, a $C_4$-$C_8$alkene-1,2-diol, or a $C_4$-$C_8$alkyne-1,2-diol. Representative examples of a $C_4$-$C_8$alkane-1,2-diol include, but are not limited to, 1,2-hexanediol, 1,2-heptanediol, 1,2-octanediol, 1,2-pentanediol, 1,2-butanediol, 4-methylpentane-1,2-diol, 4-methylhexane-1,2-diol, and 5-methylhexane-1,2-diol. Representative examples of a $C_4$-$C_8$alkene-1,2-diol include, but are not limited to, 3-butene-1,2-diol, hex-4-ene-1,2-diol and hept-5-ene-1,2-diol. Representative examples of a $C_4$-$C_8$alkyne-1,2-diol include, but are not limited to, hept-4-yne-1,2-diol and 6-methylhept-4-yne-1,2-diol. A "$C_4$-$C_8$aliphatic-1,2,3-triol," as used herein refers to a $C_4$-$C_8$alkane-1,2,3-triol, a $C_4$-$C_8$alkene-1,2,3-triol, or a $C_4$-$C_8$alkyne-1,2,3-triol. Representative examples of a $C_4$-$C_8$alkane-1,2,3-triol include, but are not limited to, 4-methylpentane-1,2,3-triol, 1,2,3-hexanetriol, 1,2,3-heptanetriol, 1,2,3-octanetriol, 1,2,3-pentanetriol, and 1,2,3-butanetriol. Representative examples of a $C_4$-$C_8$alkene-1,2,3-triol include, but are not limited to, 4,5-dideoxy-D-erythro-pent-4-enitol (pent-4-ene-1,2,3-triol), hex-4-ene-1,2,3-triol and hept-4-ene-1,2,3-triol. Representative examples of a $C_4$-$C_8$alkyne-1,2,3-triol include, but are not limited to, hept-4-yne-1,2,3-triol and oct-6-yne-1,2,3-triol.

$C_4$-$C_8$aliphatic-1,2-diols and $C_4$-$C_8$aliphatic-1,2,3-triols are available from commercial sources or may be synthesized using methods and techniques well known in the art. For example, alkane diols may be synthesized by dihydroxylation of terminal alkenes such as 4-methylpent-1-ene, 4-methylhex-1-ene, or 5-methylhex-1-ene. Likewise, alkane triols may be synthesized by dihydroxylation of primary allylic alcohols such as 4-methylpent-2-en-1-ol. The foregoing dihydroxylation reactions may be carried out using common reagents like osmium tetraoxide with or without a co-oxidant (e.g., N-methylmorpholine N-oxide). Alternatively, dihydroxylation may be accomplished by epoxidation of an olefinic bond following by ring opening of the epoxide with a molecule of water.

A first aspect of the invention provides a method of treating muscle spasms by administering a therapeutically effective amount of one or more antispasmodic agents selected from the group consisting of a $C_4$-$C_8$aliphatic-1,2-diol and a $C_4$-$C_8$aliphatic-1,2,3-triol. For example, the antispasmodic agents may be selected from a $C_4$-$C_8$alkane-1,2-diol, a $C_4$-$C_8$alkene-1,2-diol, a $C_4$-$C_8$alkyne-1,2-diol, $C_4$-$C_8$alkane-1,2,3-triol, a $C_4$-$C_8$alkene-1,2,3-triol, or a $C_4$-$C_8$alkyne-1,2,3-triol. In certain embodiments of the method, the one or more antispasmodic agents are selected from the group consisting of a $C_4$-$C_8$alkane-1,2-diol (e.g., 1,2-butanediol, 1,2-hexanediol, 1,2-octanediol) and a $C_4$-$C_8$alkane-1,2,3-triol (e.g., 1,2,3-pentanetriol, 1,2,3-hexanetriol, 1,2,3-heptanetriol). In other embodiments, the administration of one or more antispasmodic agents comprises administration of a $C_4$-$C_8$alkane-1,2-diol and a $C_4$-$C_8$alkane-1,2,3-triol. For example, muscle spasms may be treated by administration of 1,2-hexanediol and 1,2,3-hexanetriol. In other embodiments, administration of the one or more antispasmodic agents comprises administration of one $C_4$-$C_8$alkane-1,2-diol or administration of more than one $C_4$-$C_8$alkane-1,2-diol. For example, 1,2-hexanediol may be administered with or without another diol such as 1,2-butanediol. In another embodiment, administration of the one or more antispasmodic agents comprises administration of one $C_4$-$C_8$alkane-1,2,3-triol or administration of more than one $C_4$-$C_8$alkane-1,2,3-triol. For example, 1,2,3-hexanetriol may be administered with or without another triol such as 1,2,3-heptanetriol. In yet other embodiments, a single antispasmodic $C_4$-$C_8$alkane-1,2-diol such as 1,2-hexanediol may be administered to a patient. In still other embodiments, a single antispasmodic agent may be a $C_4$-$C_8$alkane-1,2,3-triol, such as 1,2,3-hexanetriol. Administration of more than one antispasmodic agents may be simultaneous or there may be some interval between administration of the agents.

Treatment of muscle spasms according to the first aspect of the invention includes administering pharmaceutical compositions having about 0.5 to about 20% (w/w) of one or more antispasmodic diols or triols, or a mixture thereof. For example, pharmaceutical compositions may have a total of about 0.5 to about 20% of one or more antispasmodic agents selected from a $C_4$-$C_8$aliphatic-1,2-diol and a $C_4$-$C_8$aliphatic-1,2,3-triol. Alternatively, pharmaceutical compositions may have a total of about 0.5 to about 20% of one or more antispasmodic agents selected from a $C_4$-$C_8$alkane-1,2-diol and a $C_4$-$C_8$alkane-1,2,3-triol. In an exemplary embodiment, pharmaceutical compositions may have about 0.5 to about 20% of a single antispasmodic agent selected from a $C_4$-$C_8$alkane-1,2-diol and a $C_4$-$C_8$alkane-1,2,3-triol. For example, pharmaceutical compositions may have about 0.5 to about 20% of a single $C_4$-$C_8$alkane-1,2-diol (e.g., 1,2-hexanediol), or a single $C_4$-$C_8$alkane-1,2,3-triol (e.g., 1,2,3-hexanetriol). Other exemplary pharmaceutical compositions may alternatively have about 0.5 to about 20% of: two $C_4$-$C_8$alkane-1,2-diols (e.g., 1,2-hexanediol, 1,2-butanediol); two $C_4$-$C_8$alkane-1,2,3-triols (e.g., 1,2,3-hexanetriol, 1,2,3-heptanetriol); or one $C_4$-$C_8$alkane-1,2-diol with one $C_4$-$C_8$alkane-1,2,3-triol. Additional diols or triols may optionally be present.

Generally, the pharmaceutical compositions used to treat muscle spasms have about 0.5 to about 20% of one or more antispasmodic diols or triols as described herein. In certain embodiments, the pharmaceutical compositions used to treat muscle spasms have one or more antispasmodic diols or triols in concentrations of about 1 to about 14%, about 1 to about 10%, about 1 to about 5%, about 1%, about 5%, about 10%, about 14%, or about 20%. As described generally above, either a single antispasmodic agent or more than one antispasmodic agents together may be present in the indicated percentages. The foregoing concentration ranges are suitable in formulations for either topical administration or systemic administration (e.g., oral, injection). In a preferred embodiment, the antispasmodic diols and triols are administered topically In certain embodiments, the antispasmodic diols and triols may be administered with one or more non-steroidal anti-inflammatory drugs (NSAID) and/or steroidal agents, such as various anti-inflammatory corticosteroids, prednisone and/or pharmaceutically acceptable excipients to relieve the spasms associated with pain. The antispasmodic diols or triols may be administered in the same pharmaceutical composition with an NSAID or corticosteroid or the drugs may be administered in different pharmaceutical compositions. For example, the diols or triols may be administered topically together with an anti-inflammatory agent in the same formulation or the drugs may be administered topically in separate formulations. Alternatively, the antispasmodic diols/triols may be administered topically whereas the anti-inflammatory agent is administered orally, or vice versa. If the antispasmodic diols/triols are administered in a separate formulation from the anti-inflammatory agent, the administrations may be at about the same time or there may be some interval of time between administrations. In a preferred embodiment, the antispasmodic diols and triols are administered topically with an NSAID.

Suitable NSAIDs for administration with the antispasmodic diols and triols include, but are not limited to, diclofenac, piroxicam, nimesulide, ketoprofen, ibuprofen, and methyl salicylate. Suitable anti-inflammatory corticosteroids include, but are not limited to, prednisone, prednisolone, cortisone, hydrocortisone, betamethasone, etc. Administration of NSAIDs or corticosteroids may be by routes of administration and in dosages and formulations as are well-known to effectively reduce inflammation. For example, diclofenac may be administered using Voltaren® gel, which contains 1% diclofenac.

In another aspect of the invention, the anti-spasmodic diols/triols may be administered in combination with anti-inflammatory agent(s) and appropriate muscle relaxants, such as metaxalone, or cyclobenzaprine hydrochloride to relieve pain or inflammation or muscular spams or actinic keratosis or arthritis or all of these or related conditions. In a preferred embodiment, the diol or triol compound, and/or anti-inflammatory agent and/or muscle relaxing agent are formulated in a topical, oral (solid or liquid) or injectable dosage form.

In another aspect of the invention is provided a method of treating conditions such as bone loss, weight gain, arthritis or autoimmune diseases like lupus by administering vitamin $D_3$ and one more $C_4$-$C_8$ aliphatic-1,2-diols and/or $C_4$-$C_8$ aliphatic-1,2,3-triols as described generally herein. The hydroxyl groups of these diols or triols may form hydrogen bonds with the hydroxyl group of vitamin $D_3$ and help absorption (orally and topically) and transport (delivery to site of action) of vitamin $D_3$.

In yet another aspect of the invention is provided a method of treating muscle spasm and bone loss, weight gain, arthritis or autoimmune diseases like lupus by administering vitamin $D_3$ and one more $C_4$-$C_8$ aliphatic-1,2-diols and/or $C_4$-$C_8$ aliphatic-1,2,3-triols as described generally herein. The $C_4$-$C_8$ aliphatic-1,2-diols and/or $C_4$-$C_8$ aliphatic-1,2,3-triols may perform the dual function of suppressing muscle spasms and facilitating the delivery of the vitamin $D_3$ to the site of action.

Another aspect of the invention provides pharmaceutical compositions comprising about 0.5 to about 20% of one or more of a $C_4$-$C_8$ aliphatic-1,2-diol, a $C_4$-$C_8$ aliphatic-1,2,3-triol, or mixtures thereof together with one or more pharmaceutically acceptable carriers. The pharmaceutical compositions of the invention may have $C_4$-$C_8$ aliphatic-1,2-diols and $C_4$-$C_8$ aliphatic-1,2,3-triols in a range of concentrations, as described hereinabove, together with one or more pharmaceutically acceptable carriers. For example, in some embodiments, a pharmaceutical composition comprises 0.5 to about 20%, about 1 to about 14%, about 1 to about 10%, about 1 to about 5%, about 1%, about 5%, about 10%, about 14%, or about 20% of a $C_4$-$C_8$ alkane triol or a $C_4$-$C_8$ alkane triol with a $C_4$-$C_8$ alkane diol, together with a pharmaceutically acceptable carrier. In further exemplary embodiments, a pharmaceutical composition comprises about 0.5 to about 20%, about 1 to about 14%, about 1 to about 10%, about 1 to about 5%, about 1%, about 5%, about 10%, about 14%, or about 20% of one or more of 1,2,3-butanetriol, 1,2,3-pentanetriol, 1,2,3-hexanetriol, 1,2,3-heptanetriol, or 1,2,3-octanetriol alone or any of the foregoing triols in combination with 1,2-butanediol, 1,2-pentanediol, 1,2-hexanediol, 1,2-heptanediol, 1,2-octanediol, together with a pharmaceutically acceptable carrier.

The term "pharmaceutically acceptable carrier" as used herein, means a non-toxic, inert solid, semi-solid or liquid filler, diluent, encapsulating material or formulation auxiliary of any type. For example, the pharmaceutical compositions may include a variety of pharmaceutically acceptable excipients such as disintegrants, surfactants, emulsifiers, gelling agents, thickening agents, emollients, binders, fillers, humectants, lubricants, glidants, buffering agents, chelating agents, tonicity agents, stabilizing agents, permeation enhancers, antioxidants, pH adjusting agents and natural and synthetic waxes etc. Particular excipients include, but are not limited to, propylene glycol, Carbomer 940, triethanolamine, glycerin, polyoxy 20 cetostearyl ether, anhydrous lanolin, glyceryl monostearate, sorbitan trioleate, sorbitan tristearate, isopropyl alcohol, water, povidone, anhydrous colloidal silica, microcrystalline cellulose, sodium starch glycolate, lactose monohydrate, starch, and magnesium stearate.

In certain embodiments, a pharmaceutical composition for topical administration to treat muscle spasms associated with pain and/or inflammation comprises a therapeutically effective amount of a non-steroidal anti-inflammatory drug together with one or more of a $C_4$-$C_8$ alkane-1,2-diol and/or a $C_4$-$C_8$ alkane-1,2,3-triol, which may be present in the percentages specified elsewhere herein. In other embodiments, a pharmaceutical composition for topical administration to treat muscle spasms associated with pain and/or inflammation comprises about 0.5 to about 20% of a non-steroidal anti-inflammatory drug together with one or more of a $C_4$-$C_8$ alkane-1,2-diol and/or a $C_4$-$C_8$ alkane-1,2,3-triol in the percentages specified elsewhere herein. Particular embodiments include about 1% diclofenac; about 5% or about 10% ibuprofen; about 0.5% piroxicam; about 2.5%, about 10%, or about 20% ketoprofen; about 1%, 2%, or 3% nimesulide. Thus, for example, a pharmaceutical composition according to the invention may comprise about 1% diclofenac; about 5% or about 10% ibuprofen; about 0.5% piroxicam; about 2.5%, about 10%, or about 20% ketoprofen; or about 1%, 2%, or 3% nimesulide with about 0.5 to about 20%, about 1 to about 14%, about 1 to about 10%, about 1 to about 5%, about 1%, about 5%, about 10%, about 14%, or about 20% of one or more of a $C_4$-$C_8$ alkanediol and/or a $C_4$-$C_8$ alkane triol. According to the foregoing compositions and percentages, the one or more $C_4$-$C_8$ alkane-1,2-diol and/or $C_4$-$C_8$ alkane1,2,3-triol may be selected from 1,2-butanediol, 1,2-pentanediol, 1,2-hexanediol, 1,2-heptanediol, 1,2-octanediol, 1,2,3-butanetriol, 1,2,3-pentanetriol, 1,2,3-hexanetriol, 1,2,3-heptanetriol, and 1,2,3-octanetriol.

In other embodiments, a pharmaceutical composition for topical administration comprises about 1% of a non-steroidal anti-inflammatory drug (e.g., diclofenac) together with 0.5 to about 20%, about 1 to about 14%, about 1 to about 10%, about 1 to about 5%, about 1%, about 5%, about 10%, about 14%, or about 20% of one or more of a $C_4$-$C_8$ alkane triol (e.g., 1,2,3-butanetriol, 1,2,3-pentanetriol, 1,2,3-hexanetriol, 1,2,3-heptanetriol, or 1,2,3-octanetriol) or any of the foregoing triols in combination with 1,2-butanediol, 1,2-pentanediol, 1,2-hexanediol, 1,2-heptanediol, 1,2-octanediol.

In one exemplary embodiment, muscle spasms may be treated by topically administering a pharmaceutical composition comprising about 1% diclofenac or salt thereof together with about 5% of 1,2-hexane diol.

In another exemplary embodiment, a pharmaceutical composition comprises about 0.5 to about 20% 1,2,3-hexanetriol and about 0.5 to about 20% of a non-steroidal anti-inflammatory drug.

The foregoing pharmaceutical compositions for topical administration may also include about 2 to about 10% of one or more surfactants or emulsifiers; about 1-5% of a gelling agent; and/or about 1-5% of a humectant.

Pharmaceutical compositions comprising one or more antispasmodic diols or triols may be topically applied with a sufficient amount of the composition (e.g., in the form of a gel) to cover the affected area. The topical application may be up to three or four times per day or as needed. The actual amount applied may vary depending on the severity of the condition and the particular patient.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

The compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to compounds described herein, stabilizers, preservatives, excipients and the like. The preferred lipids are natural and synthetic phospholipids and phosphatidyl cholines (lecithins) used separately or together. Methods to form liposomes are known in the art. See, for example, Prescott, Ed., Methods in Cell Biology, Volume XIV, Academic Press, New York, N.Y. (1976), p. 33 et seq.

In certain embodiments, a pharmaceutical composition for oral administration to treat muscle spasms associated with pain and/or inflammation comprises a therapeutically effective amount of a non-steroidal anti-inflammatory drug together with one or more of a $C_4$-$C_8$alkane-1,2-diol and/or a $C_4$-$C_8$alkane-1,2,3-triol in the percentages specified elsewhere herein. Therapeutically effective amounts of oral diclofenac, piroxicam, nimesulide, ketoprofen, are ibuprofen are well known to those skilled in the art. For example, in one embodiment an oral pharmaceutical composition comprises about 10% diclofenac with about 20% 1,2,3-hexane triol. Oral compositions may additionally include about 1-5% of a lubricant or glidant; about 15-50% of a disintegrant; or about 15-50% of a filler or binder.

Certain of the antispasmodic agents listed above have some antimicrobial properties, e.g., 1,2 hexanediol, 1,2 heptanediol and 1,2 octanediol. So when these active ingredients are used as antispasmodic agents, the need for antimicrobial agents (preservatives) in the pharmaceutical formulations will be reduced significantly or eliminated.

The phrase "therapeutically effective amount" of the present compositions means sufficient amounts of the compositions to treat disorders, at a reasonable benefit/risk ratio applicable to any medical treatment. It is understood, however, that the total daily dosage of the compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer. In particular, the treatment of chronic painful conditions may require such repeated or chronic administration of the compounds.

EXAMPLES

The compositions of the present inventions described in the following examples illustrate specific embodiments of the compositions of the present inventions. However, these examples are not intended to be limiting thereof. Several modifications can be undertaken by a person skilled in art, without departing from spirit and scope of the invention.

Example I

Topical Gel

| Topical Gel | |
|---|---|
| Ingredient | % w/w |
| Diclofenac Sodium | 1 |
| 1,2 hexanediol | 5 |
| Propylene glycol | 5 |
| Carbomer 940 | 1.3 |
| Triethanol amine | 0.7 |
| Glycerin | 5 |
| Polyoxyl 20 cetostearyl ether | 1 |
| Anhydrous Lanolin | 1 |
| Glyceryl monostearate | 1.5 |
| Sorbitan trioleate | 1 |
| Sorbitan tristearate | 0.5 |
| Isopropyl alcohol | 25 |
| Purified water | 52 |

Phase I

In the main tank, add the required amount of the purified water. Add carbomer 940 in it and heat the water to 75° C. Stir the mixture for 1 hour to fully hydrate the carbomer 940. After 1 hour of mixing, add 1,2-hexanediol, propylene glycol and glycerin. Maintain the temperature at 75° C.

Phase II

In a secondary tank, add poloxyl 20 cetostearyl ether, anhydrous lanolin, glyceryl monostearate, sorbitan trioleate and sorbitan tristearate. Heat the mixture to 75° C. and mix it well.

Transfer the mixture of phase II into the main tank containing Phase I and mix the contents well, while maintaining the temperature of 75° C. After 30 minutes of mixing, add triethanolamine and diclofenac sodium. Discontinue the heat and begin cooling. Once the temperature reaches 35° C., add isopropyl alcohol and continue stirring. Once the gel reaches room temperature of around 25° C., adjust the total weight with water, if needed and stir well. Package the product as appropriate.

Example II

Oral Tablet

| Oral Tablet | | |
|---|---|---|
| Ingredient | mg/tablet | % w/w |
| Diclofenac sodium | 50 | 10 |
| 1,2,3 hexanetriol | 100 | 20 |
| Povidone | 15 | 3 |
| Silica colloidal anhydrous | 25 | 5 |
| Microcrystalline cellulose | 40 | 8 |
| Sodium starch glycolate | 50 | 10 |
| Lactose monohydrate | 100 | 20 |
| Maize starch | 115 | 23 |
| Magnesium stearate | 5 | 1 |

Prepare a dry blend of all the ingredients listed above, except magnesium stearate in a pharmaceutically acceptable manner. Mix the blend for 30 minutes in a suitable mixture. After 30 minutes of mixing, stop the blender and add magnesium stearate. Mix for an additional 5 minutes. Compress the tablets in an appropriate tableting machine.

Example III

Alleviation of Muscle Spasms

The effect of 1,2-hexanediol to treat muscle spasms was studied in 10 patients in whom Voltaren® Gel (diclofenac sodium) alone was ineffective to relieve the muscle spasms associated with pain or inflammation. In this study, a recommended amount of Voltaren® Gel (diclofenac sodium) was mixed with 5% w/w 1,2-hexanediol and topically applied, according to the instructions for Voltaren®, to an area experiencing muscle spasms and pain and/or inflammation. Seven of the 10 patients treated with the composition of 5% w/w 1,2-hexanediol in Voltaren® Gel experienced relief of the muscle spasms.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. Furthermore, the advantages described above are not necessarily the only advantages of the discovery, and it is not necessarily expected that all of the described advantages will be achieved with every embodiment of the discovery.

What is claimed is:

1. A method of treating muscle spasms comprising administering topically to a patient in need thereof a therapeutically effective amount of a pharmaceutical composition comprising about 0.5% to about 20% (w/w) of one or more antispasmodic agents independently selected from the group consisting of a $C_4$-$C_8$ aliphatic-1,2-diol and a $C_4$-$C_8$ aliphatic-1,2,3-triol.

2. The method of claim 1 wherein the one or more antispasmodic agents are independently selected from the group consisting of a $C_4$-$C_8$ alkane-1,2-diol and a $C_4$-$C_8$ alkane-1,2,3-triol.

3. The method of claim 2 wherein the one or more antispasmodic agents are independently selected from a $C_4$-$C_8$ alkane-1,2-diol.

4. The method of claim 2 wherein the one or more antispasmodic agents are independently selected from a $C_4$-$C_8$ alkane-1,2,3-triol.

5. The method of claim 2 wherein the one or more antispasmodic agents are independently selected from a group of diols consisting of 1,2-butanediol, 1,2-pentanediol, 1,2-hexanediol, 1,2-heptanediol, and 1,2-octanediol.

6. The method of claim 2 wherein the one or more antispasmodic agents are independently selected from a group of triols consisting of 1,2,3-butanetriol, 1,2,3-pentanetriol, 1,2,3-hexanetriol, 1,2,3-heptanetriol, and 1,2,3-octanetriol.

7. The method of claim 2, wherein the patient suffers from pain and/or inflammation associated with a muscle spasm, said method further comprising the administration of a therapeutically effective amount of a non-steroidal anti-inflammatory drug or pharmaceutically acceptable salt thereof.

8. The method of claim 2, wherein the patient suffers from pain and/or inflammation associated with a muscle spasm, said method further comprising the administration of a therapeutically effective amount of one or more non-steroidal anti-inflammatory drugs or one or more steroidal compounds.

9. The method of claim 3, wherein the patient suffers from pain and/or inflammation associated with a muscle spasm, said method further comprising the administration of a therapeutically effective amount of a non-steroidal anti-inflammatory drug or pharmaceutically acceptable salt thereof.

10. The method of claim 4, wherein the patient suffers from pain and/or inflammation, said method further comprising the administration of a therapeutically effective amount of a non-steroidal anti-inflammatory drug or pharmaceutically acceptable salt thereof.

11. The method of claim 7 wherein the non-steroidal anti-inflammatory drug is selected from the group consisting of diclofenac, piroxicam, nimesulide, ketoprofen, ibuprofen, and methyl salicylate or a pharmaceutically acceptable salt thereof and the one or more antispasmodic agents are independently selected from the group consisting of 1,2-butanediol, 1,2-pentanediol, 1,2-hexanediol, 1,2-heptanediol, 1,2-octanediol, 1,2,3-butanetriol, 1,2,3-pentanetriol, 1,2,3-hexanetriol, 1,2,3-heptanetriol, and 1,2,3-octanetriol.

12. The method of claim 11 wherein the non-steroidal anti-inflammatory drug is diclofenac and the one or more antispasmodic agents are independently selected from 1,2-hexanediol and 1,2,3-hexanetriol.

13. The method of claim 11 wherein the non-steroidal anti-inflammatory drug and the one or more antispasmodic agents are administered topically.

14. The method of claim 13 wherein the non-steroidal anti-inflammatory drug is diclofenac.

15. The method of claim 14 wherein the pharmaceutical composition comprises about 1% to about 14% of the one or more antispasmodic agents and about 1% of the diclofenac.

16. The method of claim 1, wherein the antispasmodic agent is administered without an anti-inflammatory agent.

17. The method of claim 3, wherein the $C_4$-$C_8$ alkane-1,2-diol is 1,2-hexanediol.

* * * * *